United States Patent [19]
Boyd et al.

[11] Patent Number: 5,763,689
[45] Date of Patent: Jun. 9, 1998

[54] CIS-DIHYDROXYCYCLOHEXADIENES AND THEIR PREPARATION

[76] Inventors: Derek R. Boyd, David Keir Building, Belfast, United Kingdom, BT9 5AG; Howard Dalton, University of Warwick Dept. of Biological Sciences, Coventry, United Kingdom, CV4 7AL

[21] Appl. No.: 605,145

[22] PCT Filed: Sep. 7, 1994

[86] PCT No.: PCT/GB94/01940

§ 371 Date: Feb. 29, 1996

§ 102(e) Date: Feb. 29, 1996

[87] PCT Pub. No.: WO95/07253

PCT Pub. Date: Mar. 16, 1995

[30] Foreign Application Priority Data

Sep. 7, 1993 [GB] United Kingdom ............... 9318564

[51] Int. Cl.$^6$ .................................................. C07C 35/08
[52] U.S. Cl. .................................... 568/832; 568/823
[58] Field of Search ............................. 568/832, 823

[56] References Cited

U.S. PATENT DOCUMENTS 5,306,846  4/1994  Hudlicky et al. ................ 568/832

OTHER PUBLICATIONS

Hudlicky et al; Tetrahedron Asymmetry; vol. 3, #2, pp. 217–220, 1992.
Ziffer et al; JACS; 95: 12; pp. 4048–4049, 1973.
Hudlicky et al; JACS; 110: 14; pp. 4735–4741.
Robert et al; Biomed.Environ.Mass.Spectrom.;18(1);pp. 27–47, 1989.
Nakatsu et al; Drug.Metab.Dispos.;11(5);463–70, 1983.
Sigrun et al; Adv.Exp.Med.Biol.;136A(Biol.React.Intermed.2,Chem.Mech.Biol.Eff.Pt.A)387–93, 1982.
Robert et al; Toxicol.Environ.Chem.;10(3),225–46, 1985.
Billings etal; Drug.Metab.Dispos.;13(3);287–90, 1985.
Dankovic et al; Mol.Pharmacol.;27(2),287–95, 1985.

*Primary Examiner*—Gary Geist
*Assistant Examiner*—Sreeni Padmanabhan
*Attorney, Agent, or Firm*—Kirsten A. Anderson

[57] ABSTRACT

This application relates to 3-substituted and 4-substituted cis-diols. Specifically, there are provided 3-substituted diols of formula (II) and 4-substituted cis-diols having (1S, 2R) and (1R, 2S) absolute configurations of formulae (III) and (IV). Also provided are processes For making such 3- and 4-substituted cis-diols using a reductive fission reaction. The compounds described herein are useful as synthons for the preparation of various compounds including therapeutics, agricultural, polymers and other classes of compounds. In formulae (II, III and IV), R is halogen, CN, aryl alkyl, alkenyl alkynyl O-alkyl, $CF_3$ or $NO_2$.

7 Claims, No Drawings

CIS-DIHYDROXYCYCLOHEXADIENES AND THEIR PREPARATION

This is the U.S. National Stage Application of PCT/GB94/01940 filed Sep. 7, 1994 now WO95/07253 published Mar. 16, 1995.

TECHNICAL FIELD

The present invention relates to 3-substituted cis-diols and methods for their preparation.

CROSS-REFERENCE TO RELATED APPLICATIONS

This application claims priority from UK patent application 9318564.3 filed Sep. 7, 1993, which is incorporated herein by reference in its entirety.

BACKGROUND OF THE INVENTION cis-Dihydroxycyclohexadienes are formed as reaction products from the oxidation of aromatic compounds by bacterial aromatic hydrocarbon dioxygenases. This enzymatic reaction proceeds by the insertion of both atoms of molecular oxygen into the aromatic nucleus to form a vicinal cis-dihydrodiol. For substrates such as toluene, ethylbenzene, chlorobenzene, trifluorobenzene and benzyl acetate [Boyd, et al., *J. Am. Chem. Soc.*, 113:666, (1991)]; bromobenzene and iodobenzene [Boyd, et al., *J. Chem. Soc. Chem Commun.*, p. 1630, (1991)] the cis-diols formed have been designated enantiomerically pure. These enantiomerically pure cis-diol reaction products constitute a series of highly useful chiral synthons which have two functionally distinguishable double bonds, two distinguishable oxygens and, in most cases, have a single removable or reactive substituent. The utility of these compounds has been demonstrated by numerous research groups. See, for example, the following: Brown and Hudlicky, *Organic Synthesis: Theory and Practice*, ed. Hudlicky, JAI Press, Greenwich, Conn., vol. 2, 1993, p. 113; Widdowson, et al., *Janssen Chimica Acta*, 1990, 8:3; Carless, *Tetrahedron: Asymm.*, 1992, p. 795; U.S. Pat. Nos. 5,200,516, 5,306,846; U.S. patent application Ser. Nos. 07/974,057, 07/060,454; the disclosure of these U.S. Patents and Applications is incorporated herein by reference.

To date all of the synthetic work done with chiral, enantiomerically pure cis-diols has been done with compounds having the Formula I, shown below, where R is a substituent other than hydrogen. If the R substituent in a compound of Formula I is hydrogen, then the compound is meso and must be asymmetrically functionalized if it is to be used for chiral synthesis. To date, only cis-diols substituted at the 3 position and of the illustrated absolute configuration have been available for synthesis.

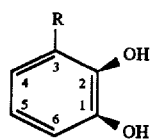
(I)

The reason for the lack of availability of enantiomerically pure cis-diols of configurations other than those shown above is due to the regiospecificity of the dioxygenase enzyme commonly used for their synthesis. Chemically, three different substituted vicinal cis-dihydroxycyclohexadiene enantiomeric pairs are possible. They are shown in Scheme 1.

Scheme 1.
Oxidation pattern of known dioxygenases with monosubstituted monocyclic aromatic compounds. R = F, Cl, Br, I, CN, CF$_3$, aryl, alkyl, alkenyl, alkynyl, O-alkyl, or NO$_2$.

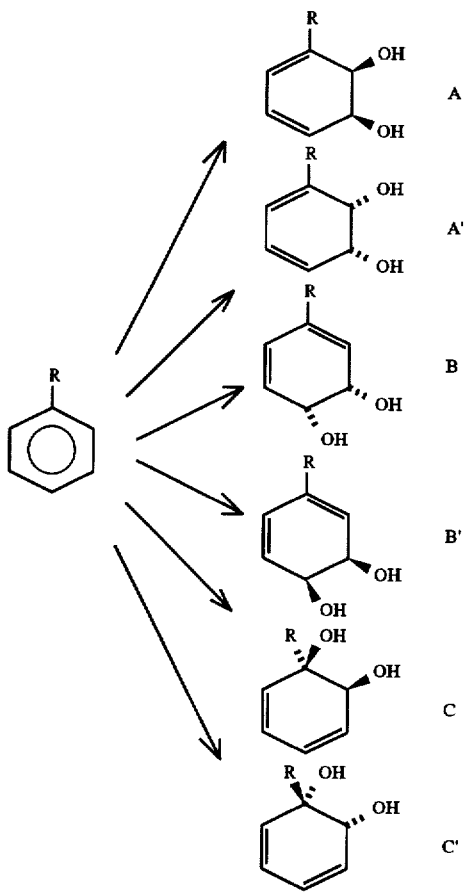

It has been reported in the literature that certain bacteria and the enzymes expressed by certain bacteria oxidize monosubstituted aromatic compounds of the type shown in the Scheme 1. Of the bacteria reported to have this activity, at least seven strains have been reported which accumulate cis-diols [Gibson, *Biochemistry*, 9:1626, (1970); Haigler, et al., *App. Environ. Microbiol.*, 57:3156, (1991); Johnston, et al., *Enzyme Microb. Technol.*, 9:706, (1987); Jenkins, et al., *Biotech. Bioeng.*, 29:873, (1987); U.S. Pat. Nos. 4,876,200; 4,927,759 and 4,508,822; EP0253485; and Geary, et al., *J. Chem. Soc. Chem. Commun.*, 1990, p. 204]. Of the chemically possible diol isomers (shown in Scheme 1), only those resulting from oxidation at the 1–2 bond are produced having the structure designated "A." These reaction products have been established to be enantiomerically pure, and have the absolute configuration illustrated.

The nature of the present invention is related to an observation that aromatic dioxygenases, reacting with disubstituted monocyclic aromatic compounds, still show a regiospecificity of dioxygenation, particularly when such dioxygenases are presented (contacted) with a substituted (preferably disubstituted) aromatic compound in which the substituents are non-identical. By "non-identical" it is meant that the two substituents differ in any number of manners, including but not limited to, size, charge, steric hindrance, hydrophobicity, etc., where size is apparently the principal factor controlling the reference point for oxygen insertion.

Size of the substituent can be determined by steric parameters such as E'$_s$, the Taft steric parameter, or u, the Charton steric parameter [Boyd, et al., *J. Chem. Soc. Chem. Commun.*, 1993, p. 974].

In the general case, there are three aromatic substitution patterns, ortho, meta, and para. Scheme 2 (below) shows the six chemically possible cis-diol regioisomers and their enantiomeric pairs which are potential reaction products from the dioxygenation of ortho disubstituted aromatic compounds.

The "D" product shown in Scheme 2 is the primary product. It can be obtained pure by fractional crystallization or any suitable method of physical or enzymatic resolution. The substituents L and S in Scheme 2 represent large (L) and small (S) substituents which exemplify the point made above, that when the dioxygenases are contacted with a disubstituted aromatic compound in which the substituents are non-identical, size appears to be the principal factor controlling the point of oxygen insertion. Without intending to be limited by any particular mechanism of action, it is believed that the large substituent (L) is apparently used by the enzyme as a reference point for the regio- and stereoselectivity. The exact same absolute configuration is reflected in the product of the disubstituted molecule as is formed in the monosubstituted product. The other products (D'-I') are shown for completeness, however, the "D" product is the primary product of the enzymatic reaction of ortho disubstituted aromatic compound.

Scheme 3 (below) shows the six chemically possible cis-diol regioisomers and their enantiomeric pairs, which are potential reaction products from the dioxygenation of meta disubstituted aromatic compounds.

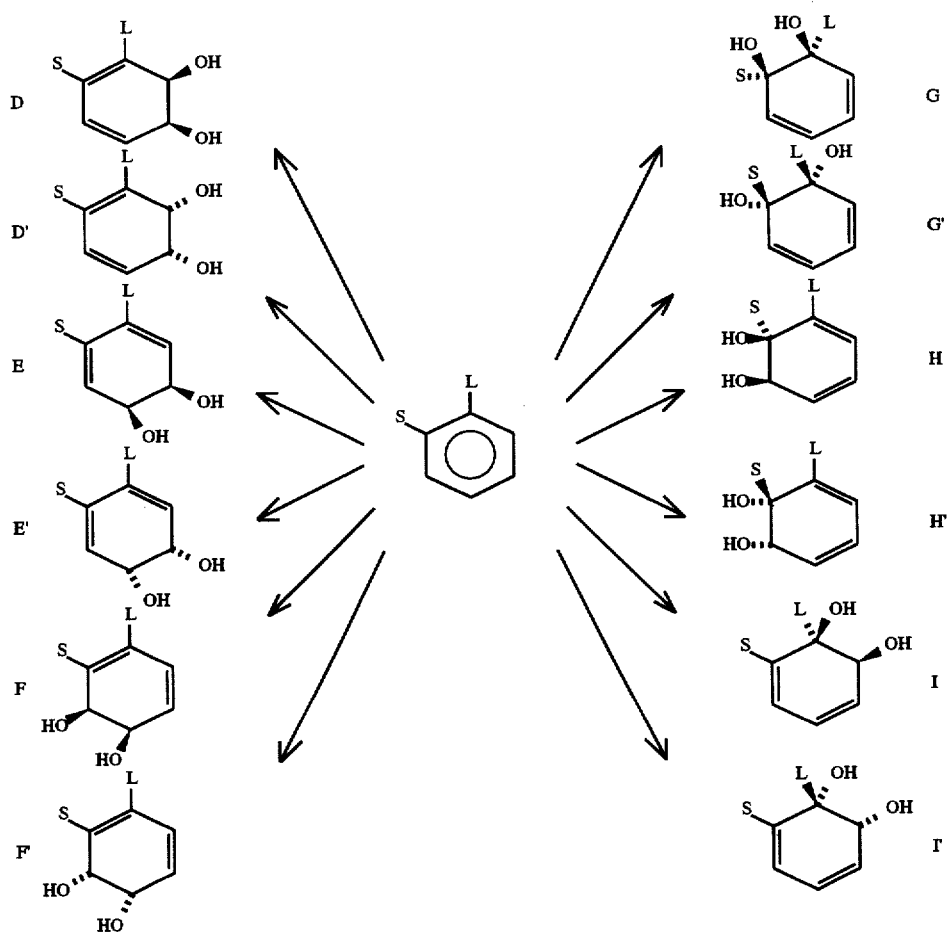

Scheme 2.
Regio and stereo selectivity of dioxygenation of ortho disubstituted aromatic compounds. L = Large substituent, S = Small substituent.

Scheme 3.
Regio and stereo selectivity of dioxygenation of meta disubstituted aromatic compounds. L = Large substituent, S = Small substituent.

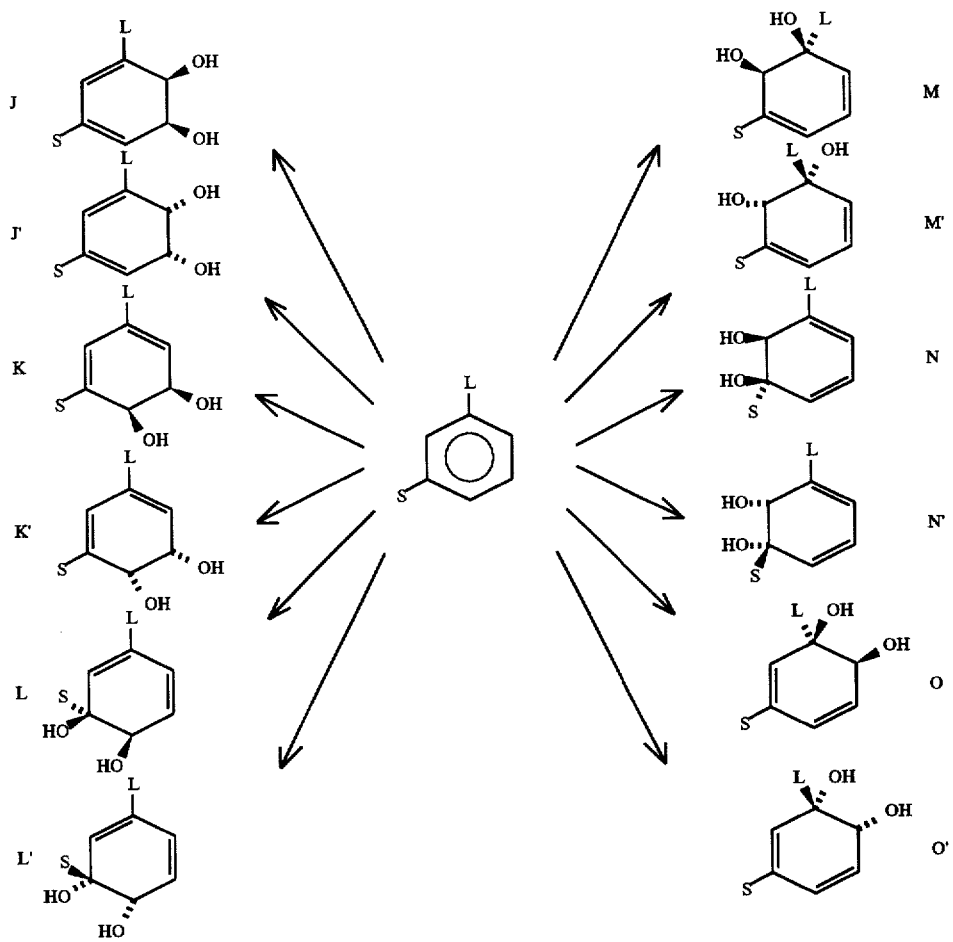

Product "J" shown in Scheme 3 is the primary product with the large substituent (L) apparently being used by the enzyme as a reference point for the regio- and stereo-selectivity. The substituents L and S as used in Scheme 3 are as defined herein. Reaction product "J" can be obtained pure by fractional crystallization or any suitable method of physical or enzymatic resolution. The exact same absolute configuration is reflected in the product of the disubstituted molecule as is formed in the monosubstituted product.

Scheme 4 (below) shows the three chemically possible cis-diol regioisomers and their enantiomeric pairs which are potential reaction products from the dioxygenation of para disubstituted aromatic compounds.

Scheme 4.
Regio and stereo selectivity of dioxygenation of para disubstituted aromatic compounds. L = Large substituent, S = Small substituent.

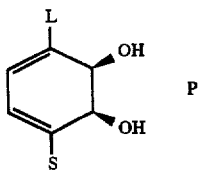

-continued
Scheme 4.
Regio and stereo selectivity of dioxygenation of para disubstituted aromatic compounds. L = Large substituent, S = Small substituent.

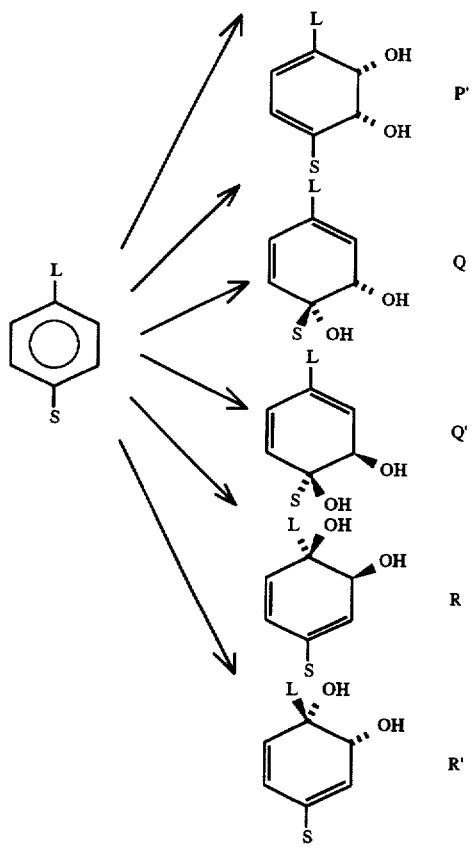

Here, both the "P" and "P'" products are observed to varying degrees, depending on the parent compound. Either compound can be obtained pure by fractional crystallization or any suitable method of physical or enzymatic resolution. The L and S substituents are as defined herein.

It is well known that various 3-substituted cis-diols having the absolute configuration shown in Formula I can be made. These 3-substituted compounds have been found to be useful synthons in making pharmaceutical compounds [Baker, W. R., Condon, S. L., *J. Org. Chem.*, 1993, 58:3277–3284; U.S. Pat. Nos. 5,200,516, 5,306,846; U.S. patent application Ser. Nos. 07/974,057, 07/060,454] and potentially as agricultural products or other specialty chemical materials such as polymers. Heretofore, although the 3-substituted cis-diols having the absolute configuration of Formula I have been described, the 3-substituted cis-diols which have the reverse absolute configuration (shown in Formula II) have not been described.

Thus, one aspect of the present invention is to provide 3-substituted cis-diols having the formula:

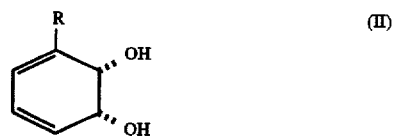

wherein R is halogen, CN, aryl, alkyl (C1–C5), alkenyl (C1–C5), alkynyl (C1–C5), O-alkyl (C1–C5, $CF_3$ or $NO_2$. The preferred substituents are halogen (Cl, Br), alkyl ($CH_3$) and alkenyl (vinyl).

Another aspect of the present invention relates to providing novel 4-substituted cis-diols, particularly 4-substituted cis-diols having the 1S,2R (Formula III) and 1R,2S (Formula IV) absolute configuration shown below:

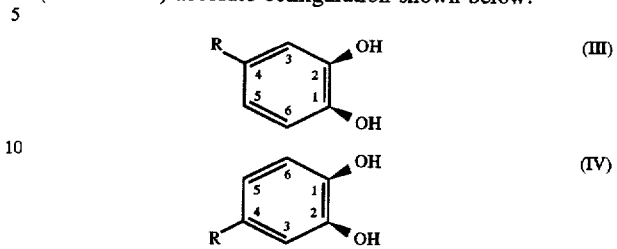

(wherein R is as defined for compounds of Formula II).

These novel compounds of the formulae II, III and IV are useful as synthons similar to the previously described 3-substituted cis-diols of Formula I. Thus far, the chemical production of these novel compounds has eluded chemists, and they are not known to be enzymatic reaction products.

SUMMARY OF THE INVENTION

In a compound embodiment of the present invention there are provided novel 3-substituted cis-diols of the formula:

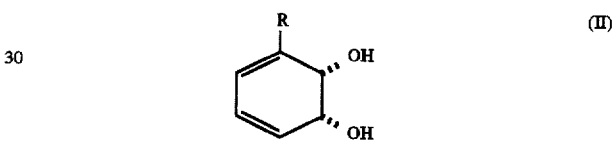

wherein R is halogen, CN, aryl, alkyl, alkenyl, alkynyl, O-alkyl, $CF_3$ or $NO_2$. The preferred substituents are halogen (Cl, Br), alkyl ($CH_3$) and alkenyl (vinyl).

In a further compound embodiment of the present invention there are provided novel 4-substituted cis-diols, particularly those having the (1S,2R) absolute configuration of the formula:

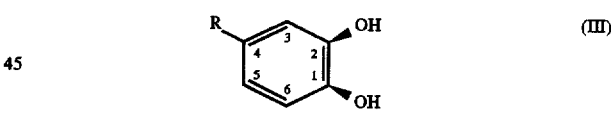

wherein R is defined as above.

Also provided are the novel 4-substituted cis-diols having the (1R,2S) absolute configuration of the formula:

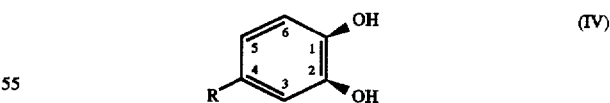

wherein R is as defined above.

These novel substituted cis-diols are related compounds heretofore not described in the literature. The compounds may be useful for a variety of purposes, preferably as synthons for subsequent synthesis of pharmaceutical, agricultural or other specialty chemicals or polymers.

In a process embodiment of the present invention the novel compounds of Formulae II, III and IV are made by selectively cleaving one substituent ($R_1$ or $R_2$) of a disubstituted cyclic aromatic compound of the formula:

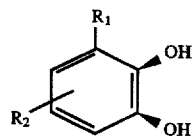
(V)

wherein $R_1$ or $R_2$ are each independently defined as halogen, CN, alkyl, alkenyl, alkynyl, aryl, O-alkyl, O-alkenyl, $CF_3$, $SR_3$, $SOR_4$, $SO_2R_5$, $SSR_6$, $SNHR_7$ or $SCR_8SR_9$, wherein $R_3$–$R_9$ are H, aryl, alkyl, alkenyl or alkynyl; provided that $R_1$ and $R_2$ are always different;

to yield a 3- or 4-monosubstituted compound of Formula II, III or IV.

In a preferred embodiment of this process aspect of the invention, the cleaving reaction is a reductive fission reaction. The substituents $R_1$ and $R_2$, which must be different, are preferably distinguished based on size, although other parameters may be relevant. $R_1$ and $R_2$, therefore, can be thought of as large and small substituents such that if $R_1$ is a large substituent, then $R_2$ is a small substituent and vice versa.

DETAILED DESCRIPTION OF THE INVENTION

We have found that one of the substituents of the disubstituted cis-diols can be selectively removed without degrading the sensitive cis-diol structure. By choosing substituents of sufficiently different reactivities, one substituent can be selectively removed by standard methods such as reductive fission to yield novel substituted cis-diols which have not been previously reported and which are not obtainable as direct products of enzymatic dioxygenation reactions. The general procedure for such selective cleavage is illustrated in Scheme 5.

The resulting substituted cis-diols are novel compounds useful as general chiral synthons, in the synthesis of, for example, carbohydrates, cyclitols, pharmaceuticals, pesticides, herbicides and other speciality materials such as polymers. The starting materials for this cleavage reaction (i.e., the ortho, meta or para disubstituted vicinal cis-diols) may be prepared by any means, chemical or enzymatic, known to those skilled in the art.

As used herein the term "large substituent" is defined relative to the term "small substituent" as measured by steric parameters. Therefore, without being limited, the large substituent may preferably be halogen, $CF_3$, $SR_3$, $SOR_4$, $SO_2R_5$, $SSR_6$, $SNHR_7$, $SCR_8SR_9$ (where $R_3$–$R_9$ is H, aryl, alkyl, alkenyl or alkynyl). On the other hand, the small substituent may preferably be halogen, CN, alkyl, alkenyl, alkynyl, aryl, O-alkyl or O-alkenyl. The alkyl, alkenyl, alkynyl substituents used herein are preferably C1–C5 carbon atoms.

As described, the disubstituted cis-diols of the present invention may be made chemically or enzymatically. When made enzymatically, acceptable enzymes include any dioxygenase enzyme, recombinant or otherwise, from any biological source which are capable of regiospecifically dioxygenating the aromatic compound on which the two substituents are not identical. Suitable enzymes include but are not limited to UV4 (Boyd, et al., *J. Chem. Soc., Perkin Trans.* 1, 1990, pp. 489–494) or JM109(pDTG601) (Zylstra and Gibson, *J. Biol. Chem.*, (1989), 264:14940).

The reductive fission reaction useful in the present invention is any reaction which breaks one or more bonds, resulting in a lower oxidation state (reduction) of the product of the reaction compared to the compound which is to be reduced. Examples of such reactions include but are not limited to reductive dehalogenation (breaks C-halogen bond); debenzylation (breaks C—O bond); hydrogenolysis, for example, with palladium and hydrogen; reduction with metal hydride, for example, tributyltin hydride, lithium aluminum hydride; reduction with reducing or dissolving

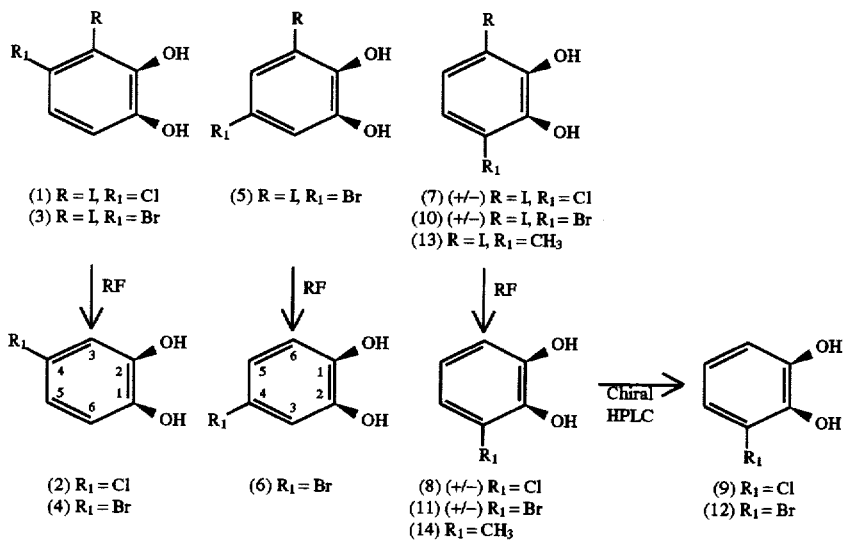

Scheme 5.
Preparation of substituted cis-diol isomers.

R = I, SX, SOX, $SO_2X$, SSX, SNHX, $SCX_2SX$;
X = H, aryl, alkyl, alkenyl, alkynyl.
$R_1$ = Halogen, CN, alkyl, alkenyl, alkynyl, aryl, O-alkyl, O-alkenyl.
RF = Reductive fission reaction (for example, by hydrogenolysis, metal hydride, etc.)

metals such as sodium; enzymatic reduction or reduction with Vitamin B12.

The following examples are not intended to limit the invention in any manner but merely are provided for purposes of illustrating the above-described invention.

EXAMPLE 1
Enzymatic Preparation of ortho Disubstituted Aromatic Compounds

Parent compounds of Formula A (shown below in Table I) which are ortho substituted aromatics were contacted with various bacterial organisms containing aromatic dioxygenase activity. The dioxygenase catalyzed biotransformation of aromatic compounds using various mutant strains of the bacterium *Pseudomonas putida* (i.e., UV4 or JM109 (pDTG601)) has been described in various publications (Gibson, D. T., et al., *Microbial Degradation of Organic Compounds*, ed. Gibson, D. T., Marcel Dekker, New York, 1984, Ch. 7, pp. 181–255; Sheldrake, G. N., *Chirality in Industry: The Commercial Manufacture and Applications of Optically Active Compounds*, eds. Collins, A. N., Sheldrake, C. N. and Crosby, J., Wiley-Interscience, New York, 1992, Ch. 6; and Boyd, D. R., et al., *J. Chem. Soc. Chem. Commun.*, 1993, pp. 974–976). The reaction products of these bacterial dioxygenations with the determined percent enantiomeric excess (% ee) are provided in Table I below. Percent enantiomeric excess can be determined either directly or indirectly by the methods described in Boyd, et al., supra, the disclosure of which is incorporated herein by reference.

TABLE I

| X | Y | ee (%) | Organism |
|---|---|--------|----------|
| I | Cl | >98 | UV4 |
| I | Cl | >98 | JM109(pDTG601) |
| I | Br | >98 | UV4 |
| I | Br | >98 | JM109(pDTG601) |

As discussed previously, these ortho disubstituted cis-diols made enzymatically or otherwise are useful starting materials for the preparation of certain 4-substituted cis-diols (1S,2R).

EXAMPLE 2
Preparation of a 4-Substituted cis-Diol of the (1S,2R) Absolute Configuration From ortho Disubstituted cis-Diol (+)-cis-(1S,2R)-1,2-Dihydroxy-4-chlorocyclohexa-3,5-diene (2)

Method A

A solution of the ortho disubstituted cis-diol (1) shown in Scheme 5 (wherein R=I and $R_1$=Cl), having greater than 98% ee as determined by the di-MTPA method described in Boyd, et al., *J. Am. Chem. Soc.*, 113:666, (1991), (1 mmol) and sodium acetate (2 mmol) in methanol (~30 ml) containing 3% palladium on carbon (10% by wt of the cis-diol), deactivated with quinoline (2–3 drops), was stirred under a hydrogen atmosphere. The progress of the reaction was monitored by TLC (silica gel; ethylacetate:hexane, 2:3). The reaction was terminated as the reaction neared completion. The monosubstituted cis-diol (2) (Scheme 5 wherein $R_1$=Cl) was separated from the unreacted disubstituted cis-diol by chromatography. The yield was 67% of theoretical. M.p.=68°–71° C. (diisopropyl ether); $[\alpha]_D^{20}$=+3.5° (c 1.0, MeOH); ee=>99% (HPLC, Boyd, et al., *J. Chem. Soc. Chem. Commun.*, 1993, p. 974); CD 260.1 nm (−0.8375), 227.1 nm (+2.247) (MeOH); MS m/z (rel. intensity) 146 ($M^+$, 45%), 100 (100%), found, $M^+$, 146.0139, cal. 146.0135; $^1$H NMR (CDCl$_3$, 500 MHz) 4.26–4.28 (m, 1H, H-2), 4.34–4.35 (m, 1H, H-1), 5.91 (dt, 1H, $J_{5,6}$ 9.9, $J_{5,3}$=$J_{5,1}$ 1.6, H-5), 6.01 (dd, 1H, $J_{6,5}$ 9.9, $J_{6,1}$ 3.3, H-6), 6.04 (dd, 1H, $J_{3,2}$ 4.7, $J_{3,5}$ 1.6, H-3).

Method B

Metal hydride reduction was used to reductively cleave the iodine from (1), Scheme 5, as described by Boyd, et al., *J. Chem. Soc. Chem. Commun.*, 1991, p. 1630, on a monosubstituted cis-diol. Compound (1) (Scheme 5, R=I and $R_1$=Cl) having a >98% ee as determined by the di-MTPA method described by Boyd, et al., *J. Am. Chem. Soc.*, 113:666, (1991), 272 mg (1.0 mmol) was dissolved in 10 ml dry acetonitrile. Tributyltin hydride, 600 μl (2.2 mmol) and azobisisobutyryl nitrile (AIBN), 181 mg (1.1 mmol) was added and the emulsion was stirred at 65° C. for 3 hours. During this time the color changed from colorless to brown and the tin hydride totally dissolved. The solvent was evaporated and the remaining material was filtered through a short (3 cm) silica gel column (diethylether). The ether phase was dried over sodium sulfate, the solvent was evaporated and the remaining material was dried under high vacuum. The yield was 100 mg (0.68 mmol), 68% of theoretical. The structure was identical to the compound in Method A above.

EXAMPLE 3
Preparation of a 4-Substituted cis-Diol of the (2S,2R) Absolute Configuration From ortho Disubstituted cis-Diols (+)-cis-(1S, 2R) -1,2-Dihydroxy-4-bromocyclohexa-3,5-diene (4)

A solution of the cis-diol (3) (Scheme 5, R=I and $R_1$=Br) having >98% ee as determined by the di-MTPA method described by Boyd, et al., *J. Am. Chem. Soc.*, 113:666, (1991), (1 mmol) and sodium acetate (2 mmol) in methanol (~30 ml) containing 3% palladium on carbon (10% by wt of the cis-diol), deactivated with quinoline (2–3 drops), was stirred under a hydrogen atmosphere. The progress of the reaction was monitored by TLC (silica gel; ethylacetate:hexane, 2:3). The reaction was terminated as the reaction neared completion. The monosubstituted cis-diol (4) (Scheme 5, $R_1$=Br) was separated from the unreacted disubstituted cis-diol by chromatography. The yield was 65% of theoretical. M.p.=67°–70° C. (diisopropyl ether); $[\alpha]_D^{20}$=+10.6° (c 1.0, MeOH); ee=>99% (HPLC, Boyd, et al., *J. Chem. Soc. Chem. Commun.*, 1993, p. 974); CD 261.2 nm (−0.5739), 228.1 nm (+3.425) (MeOH); MS m/z (rel. intensity) 190 ($M^+$, 17%), 192 (17%), 172 (30%), 174 (31%), 148 (41%), 150 (38%), 65 (100%), found, $M^+$, 189.9622, cal. 189.9622; $^1$H NMR (CDCl$_3$, 500 MHz) 4.21–4.23 (m, 1H, H-2), 4.30–4.33 (m, 1H, H-1), 5.92 (dd, 1H, $J_{6,5}$ 9.9, $J_{5,1}$ 3.4, H-6), 6.02 (dt, 1H, $J_{5,6}$ 9.9, $J_{5,3}$=$J_{5,1}$ 1.64, H-5), 6.27 (dd, 1H, $J_{3,2}$ 4.6, $J_{3,5}$ 1.5, H-3).

EXAMPLE 4
Enzymatic Preparation of meta Disubstituted Aromatic Compounds

Parent compounds of the Formula B (shown below in Table II) which are meta substituted aromatics were contacted with various bacterial organisms containing aromatic dioxygenase activity as described in Example 1 and biotransformed to the Compound B. The ee (%) was determined as described in Example 1. Results are provided in Table II.

These meta disubstituted cis-diols, made enzymatically or otherwise, are useful starting materials for making certain 4-substituted cis-diols (1R,2S).

TABLE II

| X' | Y' | ee (%) | Organism |
|---|---|---|---|
| I | Cl | >98 | UV4 |
| I | Br | >98 | JM109(pDTG601) |
| I | F | >98 | UV4 |

EXAMPLE 5

Preparation of 4-Substituted cis-diols of the (1R,2S) Absolute Configuration From m-Disubstituted cis-Diols (−)-cis-(1R,2S)-1,2-Dihydroxy-4-bromocyclohexa-3,5-diene (6)

A solution of the cis-diol (5) (Scheme 5, R=I, $R_1$=Br) having a >98% ee as determined by the di-MTPA method of Boyd, et al., *J. Am. Chem. Soc.*, 113:666, (1991), (1 mmol) and sodium acetate (2 mmol) in methanol (˜30 ml) containing 3% palladium on carbon (10% by wt of the cis-diol), deactivated with quinoline (2–3 drops), was stirred under a hydrogen atmosphere. The progress of the reaction was monitored by TLC (silica gel; ethylacetate:hexane, 2:3). The reaction was terminated as the reaction neared completion. The monosubstituted cis-diol (6) (Scheme 5, $R_1$=Br) was separated from the unreacted disubstituted cis-diol by chromatography. The yield was 65% of theoretical. M.p.= 68°–71° C. (diisopropyl ether); $[\alpha]_D^{20}$=−10.0° (C 1.0, MeOH); ee=>99% (HPLC, Boyd, et al., *J. Chem. Soc. Chem. Commun.*, 1993, p. 974).

EXAMPLE 6

Preparation of para Disubstituted Aromatic Compounds

Following the methods described in Example 1, certain para disubstituted aromatic compounds were prepared. The results and determined ee (%) are provided in Table III below.

The para disubstituted aromatic products are of variable enantiopurity as shown in Table III. These products, whether made enzymatically or otherwise, are useful in preparing the novel 3-substituted cis-diols of the present invention.

TABLE III

| X" | Y" | ee (%) | Organism |
|---|---|---|---|
| I | Cl | 15 | UV4 |
| I | Cl | 10 | JM109(pDTG601) |
| I | Br | 22 | UV4 |
| I | Br | 4 | JM109(pDTG601) |
| I | $CH_3$ | 80 | UV4 |
| I | $CH_3$ | >98 | JM109(pDTG601) |

EXAMPLE 7

Preparation of 3-Substituted cis-Diol of Low Enantiopurity From Para Disubstituted Diol cis-1,2-Dihydroxy-3-chlorocyclohexa-3,5-diene (8)

Method A

A solution of the cis-diol (7) (Scheme 5 (+/−) R=I, $R_1$=Cl) having 10% ee determined by the di-MTPA method of Boyd, et al., *J. Am. Chem. Soc.*, 113:666, (1991), (1 mmol) and sodium acetate (2 mmol) in methanol (˜30 ml) containing 3% palladium on carbon (10% by wt of the cis-diol), deactivated with quinoline (2–3 drops), was stirred under a hydrogen atmosphere. The progress of the reaction was monitored by TLC (silica gel; ethylacetate:hexane, 2:3). The reaction was terminated as the reaction neared completion. The monosubstituted cis-diol (8) (Scheme 5 (+/−) $R_1$=Cl) was separated from the unreacted disubstituted cis-diol by chromatography. The yield was 65t of theoretical, ee=10% (HPLC, Boyd, et al., *J. Chem. Soc. Chem. Commun.*, 1993, p. 974).

Method B

Metal hydride reduction was used to reductively cleave the iodine as described for a monosubstituted diol [Boyd, et al., *J. Chem. Soc. Chem. Commun.*, 1991, p. 1630]. (7) (Scheme 5 (+/−) R=I, $R_1$=Cl) having a 10% ee as determined by the di-MTPA method of Boyd, et al., *J. Am. Chem. Soc.*, 113:666, (1991), 272 mg (1.0 mmol) was dissolved in 10 ml dry acetonitrile. Tributyltin hydride, 600 µl (2.2 mmol) and azobisisobutyryl nitrile (AIBN), 181 mg (1.1 mmol) was added and the emulsion was stirred at 65° C. for 3 hours. During this time the color changed from colorless to brown and the tin hydride totally dissolved. The solvent was evaporated and the remaining material was filtered through a short (3 cm) silica gel column (diethylether). The ether phase was dried over sodium sulfate, the solvent was evaporated and the remaining material was dried under high vacuum. The yield was 110 mg (0.75 mmol), 75% of theoretical, ee=10% (HPLC, Boyd, et al., *J. Chem. Soc. Chem. Commun.*, 1993, p. 974).

EXAMPLE 8

Resolved 3-Substituted cis-Diol (−)-cis-1,2-Dihydroxy-3-chlorocyclohexa-3,5-diene (9) The resolved 3-substituted cis-diol (9) (Scheme 5, $R_1$=Cl) was prepared by separation of (8), prepared as shown in Example 7, on a chiral phase HPLC column Chiralcel OJ (Daicel Industries), isopropanol (10): hexane (90) (HPLC, Boyd, et al., *J. Chem. Soc. Chem. Commun.*, 1993, p. 974).

(−) isomer r.t.=19.1 min., (+) isomer r.t.=20.5 min., α=1.14. The identity of the (+) isomer was determined by co-injection of the authentic compound produced by reaction of chlorobenzene with toluene dioxygenase. The separated peaks were collected and their purity was confirmed by chromatography in the same system. The $^1$H NMR (DMSO, $D_6$, 300 MHz) spectra of the separated compounds were identical to each other and the authentic (+) isomer.

EXAMPLE 9
Preparation of 3-Substituted cis-Diol of Low Enantiopurity From para Disubstituted Diol (+/−)-cis-1,2-Dihydroxy-3-bromocyclohexa-3,5-diene (11) A solution of the cis-diol, (10) (Scheme 5 (+/−) R=I, $R_1$=Br) having a 4% ee as determined by the di-MTPA method of Boyd, et al., *J. Am. Chem. Soc.*, 113:666, (1991), (1 mmol) and sodium acetate (2 mmol) in methanol (~30 ml) containing 3% palladium on carbon (10% by wt of the cis-diol), deactivated with quinoline (2–3 drops), was stirred under a hydrogen atmosphere. The progress of the reaction was monitored by TLC (silica gel; ethylacetate:hexane, 2:3). The reaction was terminated as the reaction neared completion. The monosubstituted cis-diol (11) (Scheme 5 (+/−) $R_1$=Br) was separated from the unreacted disubstituted cis-diol by chromatography. The yield was 62% of theoretical. M.p.=91°–94° C. (diisopropyl ether); $[\alpha]_D^{20}$=−1.0° (c 1.0, MeOH); ee=4% (HPLC, Boyd, et al., *J. Chem. Soc. Chem. Commun.*, 1993, p. 974); MS m/z (rel. intensity) 192 ($M^+$, 30%), 190 (32%), 65 (100%); $^1$H NMR ($CDCl_3$, 300 MHz) 4.30 (d, 1H, $J_2$, 6.5, H-2), 4.5 (m, 1H, H-1), 5.91 (m, 1H, H-5), 5.97 (dd, 1H, $J_{6,5}$ 9.5, $J_{6,1}$ 3.4, H-6), 6.40 (d, 1H, H-4).

EXAMPLE 10
Resolved 3-Substituted cis-Diol (−)-cis-1,2-Dihydroxy-3-bromocyclohexa-3,5-diene (12)

The resolved 3-substituted cis-diol (12) (Scheme 5, $R_1$=Br) was prepared by separation of (11), prepared as shown in Example 9, on a chiral phase HPLC column Chiralcel OJ (Daicel Industries), isopropanol (10) : hexane (90) (HPLC, Boyd, et al., *J. Chem. Soc. Chem. Commun.*, 1993, p. 974), (−) isomer r.t.=20.1 min., (+) isomer r.t.=21.5 min., α=1.15. The identity of the (+) isomer was determined by co-injection of the authentic compound produced by reaction of bromobenzene with toluene dioxygenase. The separated peaks were collected and their purity was confirmed by chromatography in the same system. The $^1$H NMR (DMSO, $D_6$, 300 MHz) spectra of the separated compounds were identical to each other and the authentic (+) isomer.

EXAMPLE 11
Preparation of 3-Substituted cis-Diol From para Disubstituted Diol (−)-cis-1,2-Dihydroxy-3-methylcyclohexa-3,5-diene (14)

A solution of the cis-diol (13) (Scheme 5, R=I, $R_1$=$CH_3$) having a >98% ee as determined by the di-MTPA method of Boyd, et al., *J. Am. Chem. Soc.*, 113:666, (1991), (1 mmol) and sodium acetate (2 mmol) in methanol (~30 ml) containing 3% palladium on carbon (10% by wt of the cis-diol), deactivated with quinoline (2–3 drops), was stirred under a hydrogen atmosphere. The progress of the reaction was monitored by TLC (silica gel; ethylacetate:hexane, 2:3). The reaction was terminated as the reaction neared completion. The monosubstituted cis-diol (14) (Scheme 5, $R_1$=$CH_3$) was separated from the unreacted disubstituted cis-diol by chromatography. The yield was 72% of theoretical. M.p.=56°–57° C. (diisopropyl ether); $[\alpha]_D^{20}$=−24° (c 1.0, MeOH); ee>99% (HPLC, Boyd, et al., *J. Chem. Soc. Chem. Commun.*, 1993, p. 974); $^1$H NMR ($CDCl_3$, 300 MHz) 1.91 (s, 3H, Me), 4.08 (d, 1H, $J_2$, 6.0, H-2), 4.30 (m, 1H, H-1), 5.74 (d, 1H, $J_{4,5}$ 4.8, H-4), 5.80 (dd, 1H, $J_{6,5}$ 9.5, $J_{6,1}$ 3.4, H-6), 5.91 (m, 1H, H-5).

We claim:

1. A enantiomerically pure 3-substituted cis-diol having the formula:

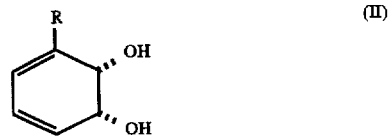

(II)

wherein R is halogen except F, CN, aryl, alkyl, alkenyl, alkynyl, O-alkyl, $CF_3$ or $NO_2$.

2. A cis-diol of claim 1 wherein R is Cl, Br, methyl or vinyl.

3. A 4-substituted cis-diol having (1S,2R) absolute configuration represented by the formula:

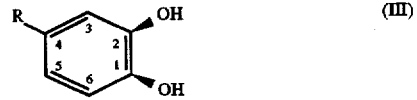

(III)

wherein R is halogen, CN, alkyl, alkenyl, alkynyl, O-alkyl, $CF_3$ or $NO_2$.

4. A cis-diol of claim 3 wherein R is Cl or Br.

5. A 4-substituted cis-diol having a (1R, 2S) absolute configuration represented by the formula:

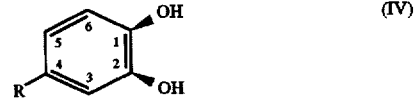

(IV)

wherein R is halogen, CN, alkyl, alkenyl, alkynyl, O-alkyl, $CF_3$ or $NO_2$.

6. A cis-diol of claim 5 wherein R is Br.

7. A process for pre-paring the compounds of any one of the preceding claims, the process comprising starting with a disubstituted cyclic diene diol of the formula:

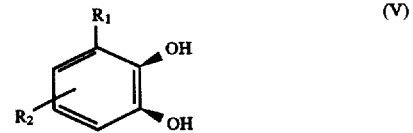

(V)

wherein $R_1$ and $R_2$ are each independently defined as halogen, CN, alkyl, alkenyl, alkynyl, aryl, O-alkyl, O-alkenyl, $CF_3$, $SR_3$, $SOR_4$, $SO2R_5$, $SSR_6$, $SNHR_7$, $SCR_3SR_9$; wherein $R_3$–$R_9$ are H, aryl, alkyl, alkenyl, or alkynyl; provided that $R_1$ and $R_2$ are always different; and subjecting the disubstituted cyclic diene diol of Formula V to a reductive fission reaction to selectively cleave $R_1$.

* * * * *